United States Patent [19]
Kais et al.

[11] Patent Number: 5,516,524
[45] Date of Patent: May 14, 1996

[54] LAXATIVE COMPOSITIONS CONTAINING BULK FIBER

[75] Inventors: Theresa M. Kais, Loveland; Paul J. Sagel, Maineville, both of Ohio

[73] Assignee: The Procter & Gamble Company, Cincinnati, Ohio

[21] Appl. No.: 170,476

[22] Filed: Dec. 20, 1993

[51] Int. Cl.$^6$ .............................. A61K 9/16; A61K 9/20; A61K 9/48; A61K 35/78
[52] U.S. Cl. .................... 424/439; 424/451; 424/464; 424/489; 424/195.1; 424/78.01; 514/892
[58] Field of Search ........................... 424/451, 439, 424/464, 489; 514/892

[56] References Cited

U.S. PATENT DOCUMENTS

| | | | |
|---|---|---|---|
| 2,764,590 | 9/1956 | Kottler et al. | 260/295 |
| 3,927,195 | 12/1975 | Messora | 424/21 |
| 4,005,196 | 1/1977 | Jandacek et al. | 424/180 |
| 4,321,263 | 3/1982 | Powell et al. | 424/195 |
| 4,459,280 | 7/1984 | Colliopoulos et al. | 424/35 |
| 4,511,561 | 4/1985 | Madaus et al. | 424/195.1 |
| 4,548,806 | 10/1985 | Colliopoulos et al. | 424/35 |
| 4,834,985 | 5/1989 | Elger et al. | 424/488 |
| 4,911,889 | 3/1990 | Leland et al. | 422/26 |
| 4,942,042 | 7/1990 | Bhargava et al. | 424/683 |
| 4,952,402 | 8/1990 | Sparks et al. | 424/419 |
| 5,034,378 | 7/1991 | Cox | 514/23 |
| 5,068,110 | 11/1991 | Fawzi et al. | 424/461 |
| 5,149,541 | 9/1992 | Leis, Jr. et al. | 424/489 |
| 5,219,570 | 6/1993 | Barbera | 424/195.1 |
| 5,229,117 | 7/1993 | Leland et al. | 424/195.1 |
| 5,232,698 | 8/1993 | Hord | 424/195.1 |
| 5,234,916 | 8/1993 | Hord | 514/57 |

FOREIGN PATENT DOCUMENTS

| | | | |
|---|---|---|---|
| 59-193816 | 11/1984 | Japan . | |
| 63-20409 | 4/1988 | Japan . | |
| 05117149 | 6/1991 | Japan | A61K 31/445 |
| 2230442 | 10/1990 | United Kingdom | A61J 3/07 |
| 2230441 | 10/1990 | United Kingdom | A61J 3/07 |
| WO91/12795 | 9/1991 | WIPO | A61K 9/22 |

OTHER PUBLICATIONS

Adels, Morton J., M.D., "Relative Efficacy of Three Laxatives In Postpartum Hospital Use", Delaware Medical Journal, (Jul. 1974), 346–349.

Anderberg, Eva Karin, Christer Nystrom and Per Artursson, "Epithelial Transport of Drugs in Cell Culture. VII: Effects of Pharmaceutical Surfactant Excipients and Bile Acids on Transepithelial Permeability in Monolayers of Human Intestinal Epithelial (Caco-2) Cells", Journal of Pharmaceutical Sciences, vol. 81, No. 9 (Sep. 1992), 879–887.

Bretagne, J. F., N. Vidon, CH L'Hirondel, and J. J. Bernier, "Increased Cell Loss in the Human Jejunum Induced by Laxatives (Ricinoleic Acid, Dioctyl Sodium Sulphosuccinate, Magnesium Sulphate, Bile Salts)", Gut. 22 (1981), 264–269.

Case, Marvin T. DVM PhD., J. Knox Smith MS and Robert A. Nelson DVM, "Acute Mouse and Chronic Dog Toxicity Studies of Danthron, Dioctyl Sodium Sulfosuccinate, Poloxalkol and Combinations", Drug and Chemical Toxicology, 1(1) (1977-78), 89–101.

Chapman, R. W., J. Sillery, D. D. Fontana, C. Matthys, and D. R. Saunders, "Effect of Oral Dioctyl Sodium Sulfosuccinate on Intake–output Studies of Human Small and Large Intestine", Gastroenterology (1985): 89; 489–93.

Curry, Clarence E., Jr., and Demetris Tatum–Butler, "Laxative Products", Handbook of Nonprescription Drugs, 10th ed. (1993), 219–225.

Donowitz, Mark, M.D. and Henry J. Binder, M.D., "Effect of Dioctyl Sodium Sulfosuccinate on Colonic Fluid and Electrolyte Movement", Gastroenterology, vol. 69, No. 4, (1975), 941–950.

Fain, Allen M., MD, Rosemary Susat, MD, Margaret Herring and Karen Dorton, "Treatment of Constipation in Geriatric and Chronically Ill Patients: A Comparison", Southern Medical Journal, 71 (1978). 677–680.

Fincher, Julian H., "Particle Size of Drugs and its Relationship to Absorption and Activity", Journal of Pharmaceutical Sciences (Nov. 1968), vol. 57, No. 11; 1825–1835.

Gaginella, T. S., PhD, J. C. Lewis, PhD, and S. F. Phillips, MD, "Rabbit Ileal Mucosa Exposed to Fatty Acids, Bile Acids, and Other Secretagogues", Digestive Diseases (Sep. 1977), vol. 22, No. 9; 781–790.

Gullikson, Gary W., Mark Sender and Paul Bass, "Laxative–Like Effects of Nonsteroidal Anti–Inflammatory Drugs on Intestinal Fluid Movement and Membrane Integrity", The Journal of Pharmacology and Experimental Therapeutics, vol. 220, No. 2 (1982), 236–242.

Jauch, R., R. Hankwitz, K. Beschke and H. Pelzer, "Bis–(p–hydroxyphenyl)–pyridyl–2–methane: The Common Laxative Principle of Bisacodyl and Sodium Picosulfate", Arzneim.–Forsch. (Drug Res.) 25, Nr. 11 (1975), 1796–1800.

Khalafallah, Nawal, M. Wafik Gouda and Said A. Khalil, "Effect of Surfactants on Absorption through Membranes IV: Effects of Dioctyl Sodium Sulfosuccinate on Absorption of a Poorly Absorbable Drug, Phenolsulfonphthalein, in Humans", Journal of Pharmaceutical Sciences, vol. 64, No. 6 (Jun. 1978), 991–994.

Kamm, M. A., J. E. Lennard Jones, D. G. Thompson, R. Sobnack, N. W. Garvie, and Marie Granowska, "Dynamic Scanning Defines a Colonic Defect in Severe Idiopathic Constipation", Gut. (1988), 29; 1085–1092.

(List continued on next page.)

Primary Examiner—Thurman K. Page
Assistant Examiner—James M. Spear
Attorney, Agent, or Firm—Douglas C. Mohl; Mary Catherine Poland; Jacobus C. Rasser

[57] ABSTRACT

An ingestible laxative composition comprising specified amounts of dioctyl sulfosuccinate and bulk fiber selected from the group consisting of psyllium, methylcellulose, polycarbophil, calcium polycarbophil, bran, malt soup extract, karaya, guar gum, and mixtures thereof, preferably in single dose form, is described.

18 Claims, No Drawings

OTHER PUBLICATIONS

Leng–Peschlow, Elke, "Effects of Sennosides A+B and Bisacodyl on Rat Large Intestine", Pharmacology (1989), 38; 310–318.

Lish, Paul M. and Kendrick W. Dungan, "Peristaltic–Stimulating and Fecal–Hydrating Properties of Dioctyl Sodium Sulfosuccinate, Danthron, and Cascara Extracts in the Mouse and Rat", American Pharmaceutical Association 47 (1958), 371–375.

Lish, Paul M., PhD., "Some Pharmacologic Effects of Dioctyl Sodium Sulfosuccinate on the Gastrointestinal Tract of the Rat", vol. 41, No. 6 (Dec. 1961), 580–584.

Lorenz, Egon, Michael B. Shimkin, Harold L. Stewart, "Preparations of Dispersions of Carcinogenic Hydrocarbons and Hormones with the Aid of Dioctyl Ester of Sodium Sulfosuccinate (Aerosol O.T.)", Journal of the National Cancer Institute, 355–360 Jan. 1939.

Lundholm, Lennart and Nils Svedmyr, "The Influence of Dioctyl Sodium Sulfosuccinate on the Laxative Action of some Anthraquinone Derivatives", Acta Pharmacol. Toxicol. 15 (1959) 373–383.

MacKenzie, K., S. Henwood, G. Foster, F. Akin, R. Davis, P. DeBaecke, G. Sisson, G. McKinney, "Three–Generation Reproduction Study with Dioctyl Sodium Sulfosuccinate in Rats", Fundamental and Applied Toxicology 15 (1990), 53–62.

Malik, Shah N., Donald H. Canaham and M. Wafik Gouda, "Effect of Surfactants on Absorption through Membranes III: Effects of Dioctyl Sodium Sulfosuccinate and Poloxalene on Absorption of a Poorly Absorbable Drug, Phenolsulfonphthalein, in Rats", Journal of Pharmaceutical Sciences, vol. 64, No. 6 (Jun. 1978), 987–990.

Moriarty, K. J., M. J. Kelly, R. Beetham and M. L. Clark, "Studies on the Mechanism of Action of Dioctyl Sodium Sulphosuccinate in the Human Jejunum", Gut. (1985), 26, 1008–1013.

Porro, G. Bianchi, M. Petrillo, A. Prada, "Endoscopy in Dypepsia", British Society for Digestive Endoscopy; Memorandum on Further National Needs for Fiberoptic Endoscopy of the Gastrointestinal Tract, British Medical Journal (Mar. 1975).

Preston, D. M., MRCP and J. E. Lennard–Jones, FRCP, "Pelvic Motility and Response to Intraluminal Bisacodyl in Slow–Transit Constipation", Digestive Diseases and Sciences, vol. 30, No. 4 (Apr. 1985), 289–294.

Roth, W. and K. Beschke, "Pharmacokinetics and Laxative Effect of Bisacodyl after Administration of Various Dosage Forms" (translation), Arzneim.–Forsch./Drug Res. V. 38(1), #4 (1988), 570–574.

Saunders, D. R., M. D., J. Sillery and D. Rachmilewitz, M.D., "Effect of Dioctyl Sodium Sulfosuccinate on Structure and Function of Rodent and Human Intestine", Gastroenterology (1975), vol. 69, No. 2; 380–386.

Sigma chemical catalogue, 1537–39 Jan. 1983.

Stewart, Ronald B., MS and Leighton E. Cluff, MD, "Gastrointestinal Manifestations of Adverse Drug Reactions", The American Journal of Digestive Diseases, vol. 19, No. 1 (Jan. 1974) 1–7.

Whistler, Roy L. and James N. BeMiller, Industrial Gums: Polysaccharides and Their Derivatives, 3rd Ed. (1993), Chapters 5–8, 13, 18, 20.

Federal Register, Department of Health, Education and Welfare, Food and Drug Administration, "Over–the–Counter Drugs–Proposed Establishment of Monographs for OTC Laxative, Antidiarrheal, Emetic and Antiemetic Products," Mar. 21, 1975, vol. 40, No. 56, Part II.

Pharmacology and Therapeutics, Grollman et al., 1970, pp. 532–537.

Facts and Comparisons, Kastrup et al., Oct. 1984, pp. 322–323c.

LAXATIVE COMPOSITIONS CONTAINING BULK FIBER

BACKGROUND OF THE INVENTION

Bulk fibers such as psyllium and methylcellulose are known effective laxatives. Bulk fiber laxatives are often powders which are mixed in water and consumed. Another type of laxative is a stimulant laxative, which is typically available in tablet or capsule form. These include senna, phenolphthalein, casanthranol, and bisacodyl.

Benefits of bulk laxatives relative to stimulant laxatives include: mildness, naturalness, minimal to no diarrhea, and/or a more normal, bulked bowel movement. However, bulk laxatives traditionally work slower than stimulant laxatives. Although stimulant laxatives can be harsh and are sometimes associated with cramping, the constipated person is often quite uncomfortable and does not want to wait the several days it may take for a bulk fiber to provide relief. Stimulant laxatives ordinarily provide overnight relief from constipation. An ideal laxative would be one which provides the benefits of bulk fiber, yet also provides speed to relief.

The active ingredient in some commercially available stool softeners is dioctyl sulfosuccinate, which is an anionic medicinal surfactant. Dioctyl sulfosuccinates combined with stimulant laxatives such as phenolphthalein, casanthranol, and senna are permitted active ingredients, according to the Federal Register, vol. 40, No. 56, Part II Over-the-Counter-Drugs, "Proposed Establishment of Monographs for OTC Laxative, Antidiarrheal, Emetic and Antiemetic Products", p. 12941. Also included therein is dioctyl sulfosuccinate (docusate sodium) in combination with sodium carboxymethylcellulose. It is believed that there is no commercially available laxative composition with both dioctyl sulfosuccinate and the bulk fibers herein as the active ingredients.

It has been found by the present invention that bulk fibers, particularly psyllium, methylcellulose, polycarbophil, calcium polycarbophil, bran, malt soup extract, karaya, guar gum, and mixtures thereof, can be combined with dioctyl sulfosuccinate to provide a laxative with surprisingly increased speed to relief. Benefits of this combination can include gentle relief, making bowel movements easier to pass, relief of constipation, causing predictable results, good signal to go, complete relief and/or a normal, bulked bowel movement.

A problem, though, with including dioctyl sulfosuccinate in ingestible laxative compositions, particularly those which are to be masticated, is the bad taste of this anionic surfactant. This bitter taste is a particular problem in laxative drink mixes, chewable tablets and food forms containing dioctyl sulfosuccinate. A process has therefore now been invented by which can been invented by which an ingestible, neutral tasting laxative composition containing dioctyl sulfosuccinate can be made.

This process has the advantage of making a composition which is effective for treating constipation, and which, even though it contains dioctyl sulfosuccinate, is not bad tasting. By this process, the encapsulated dioctyl sulfosuccinate is not tasted in the mouth, yet it is available in the gastrointestinal tract to aid in the relief of constipation.

A further advantage of this process is its use in making a dioctyl sulfosuccinate-containing composition for use as a medicinal drug which minimizes or eliminates the stomach disturbances, such as nausea, which can be side effects of taking dioctyl sulfosuccinate.

SUMMARY OF THE INVENTION

This invention relates to an ingestible laxative composition comprising, by weight of the composition: (a) from about 1% to about 99.99% of bulk fiber selected from the group consisting of psyllium, methylcellulose, polycarbophil, calcium polycarbophil, bran, malt soup extract, karaya, guar gum, and mixtures thereof; and (b) from about 0.0005% to about 25% of dioctyl sulfosuccinate.

DETAILED DESCRIPTION OF THE INVENTION

I. Composition of the Present Invention

Compositions according to the present invention include certain bulk fibers and dioctyl sulfosuccinate. Bulk forming laxatives work by increasing the water content and bulk volume of the stool, thereby promoting a bowel movement. The bulk fiber is generally not absorbed by the gastrointestinal tract. Dioctyl sulfosuccinate assists in relieving constipation. The combination is believed to work more quickly to relieve constipation than bulk fiber alone. The bulk fiber ingredient of the present compositions ordinarily is a powder which comprises the physical majority of the composition. The dioctyl sulfosuccinate is ordinarily a soft, waxy material which is present in the composition in much smaller amounts than the bulk fiber.

A. Bulk Fiber

The ingestible compositions herein comprise from about 1% to about 99.99%, preferably from about 5% to about 99%, more preferably from about 10% to about 98%, most preferably from about 15% to about 95%, by weight of the composition, of bulk fiber. For the preferred drink mix form, from about 50% to about 70%, by weight of the composition, of bulk fiber, preferably psyllium, is preferred.

Preferred bulk fibers herein are selected from the group consisting of psyllium, methylcellulose, calcium polycarbophil, polycarbophil, bran, malt soup extract, karaya, guar gum, and mixtures thereof. More preferred bulk fibers are selected from the group consisting of psyllium, sodium methylcellulose, calcium polycarbophil, polycarbophil, and mixtures thereof. Most preferred is psyllium husk. The bulk fiber herein is preferably not carboxymethylcellulose. Carboxymethylcellulose has a tendency to make smeary stools, which are difficult to wipe clean after a bowel movement.

Preferred psyllium husk for use herein comprises particle sizes distributed such that: less than about 15% is greater than about 80 mesh, at least about 45% is within the range of from about 80 mesh to about 200 mesh, and less than about 40% is smaller than about 200 mesh. This is according to U.S. Pat. No. 5,149,541, Leis, Jr. et al, issued Sep. 22, 1992, incorporated herein by reference. Most preferably, the psyllium husk is milled to a particle size no greater than 4% on 100 mesh and betwen 25% and 50% through 200 mesh.

Preferred psyllium husk for use herein is sanitized according to U.S. Pat. Nos. 4,911,889 and/or 5,229,117, Leland et al, issued Mar. 27, 1990 and Jul. 20, 1993, both incorporated herein by reference. Psyllium husk for use herein is preferably in a composition comprising hydrolyzed starch oligosaccharide, preferably maltodextrin, and is preferably sweetened with cyclamate, aspartame, saccharin or a combination thereof, according to U.S. Pat. No. 4,459,280, Colliopoulos, issued Jun. 10, 1984, incorporated herein by reference. Psyllium husk for use herein preferably comprises edible acid and is agglomerated according to U.S. Pat. No. 5,219,570, Barbera, issued Jun. 15, 1993, incorporated herein by reference. The psyllium husk preferably comprises citric acid which is uniformly dispersed throughout a maltodextrin coating, further according to Barbera. Preferably, then, the psyllium husk is agglomerated with maltodextrin and further comprises citric acid which is uniformly dispersed throughout the maltodextrin.

Preferably, psyllium husk-containing drink mixes herein comprise the divalent cation salt of strong inorganic acids selected from the group consisting of magnesium sulfate, calcium sulfate, calcium chloride, zinc sulfate, zinc chloride, and mixtures thereof, preferably magnesium sulfate. This is according to U.S. Pat. Nos. 5,232,698 and/or 5,234,916, Hord, issued Aug. 3 and 10, 1993, both incorporated herein by reference.

B. Dioctyl Sulfosuccinate

The ingestible compositions herein also comprise from about 0.0005% to about 25%, preferably from about 0.005% to about 15%, more preferably form about 0.1% to about 10%, most preferably from about 0.5% to about 5%, by weight of the composition, of dioctyl sulfosuccinate.

Preferably, the dioctyl sulfosuccinate is selected from the group consisting of dioctyl sodium sulfosuccinate, dioctyl calcium sulfosuccinate, dioctyl potassium sulfosuccinate, and mixtures thereof. Most preferred is dioctyl sodium sulfosuccinate or dioctyl calcium sulfosuccinate. This composition is preferably a single dose composition for relieving constipation.

Dioctyl sulfosuccinate is sulfosuccinic acid bis[2-ethylhexyl]ester. Sodium dioctyl sulfosuccinate is a white waxy solid producing a clear, colorless solution in alcohol.. The chemical formula for sodium dioctyl sulfosuccinate is $C_{20}H_{37}O_7SNa$.

The mechanism of action of dioctyl sodium sulfosuccinate has not been proven. Without meaning to be bound by theory, it is believed that dioctyl sodium sulfosuccinate at millimolar concentrations provides laxation by acting as an intestinal secretagogue. It is further believed that the ability of dioctyl sodium sulfosuccinate to enhance retention of luminal fluid and therefore fecal hydration may be the reason that it enhances laxation when combined with bulk fiber, particularly psyllium husk. Dioctyl sodium sulfosuccinate is not appreciably absorbed from the gastrointestinal tract.

Interestingly, dioctyl sodium sulfosuccinate is a medicinal drug which has been found to be commonly associated with gastrointestinal disturbances such as diarrhea in both hospitalized and nonhospitalized patients, according to R. Stewart and L. Cluff, "Gastrointestinal Manifestations of Adverse Drug Reactions", *The American Journal of Digestive Diseases,* Vol. 19, No. 1, pp. 1–7 (January 1974). The bulk fibers herein may reduce these gastrointestinal disturbances.

The combination of a natural stimulant laxative, casanthranol, and dioctyl sodium sulfosuccinate has been found to be significantly superior to a preparation containing another natural stimulant laxative, senna, in producing earlier stools with less straining. M. J. Adds, "Relative Efficacy of Three Laxatives in Post-Partum Hospital Use", Delaware Medical Journal, July, 1974.

C. Forms

The laxative composition herein is preferably selected from the group consisting of a drink mix, solid dose form, gel capsule form, and a food form. It is most preferably in the form of a drink mix. Food forms include wafers, bars, cookies, cereals, muffins, beverages and baked goods where moisture contents are kept at very low levels. For baked goods, it is preferred to keep the water activity ($a_w$) less than 0.5. Preferred food forms herein are wafers or bars.

Solid dose forms include tablets, liquid containing capsules, and hard or soft shelled capsules. Gel capsule forms can include hard or soft gelatins, which can be filled with dry or liquid materials.

The laxative compositions herein are preferably selected from the group consisting of drink mixes, tablets, capsules, liquicaps, wafers, and bars. They are most preferably powdered drink mixes. The most preferred drink mixes herein consist essentially of from about 4 grams to about 10 grams, most preferably from about 4.5 grams to about 6 grams, of bulk fiber, preferably psyllium husk, and from about 100 milligrams to about 500 milligrams, most preferably from about 200 milligrams to about 300 milligrams, of dioctyl sulfosuccinate, preferably calcium or sodium.

Alternatively, the compositions herein can be in two or more parts or phases, as where dioctyl sulfosuccinate is in microcapsules within or combined with the bulk fiber.

Compositions herein can be used for treatment of occasional constipation, e.g. a single dose, or for daily fiber therapy, e.g. a drink mix which is mixed with at least eight ounces of liquid and ingested one time per day each morning for no more than seven days. Single doses are preferred.

A single dose of a composition herein preferably contains from about 0.5 gram to about 100 grams, preferably from about 1 to about 10 grams, of bulk fiber, preferably psyllium husk. A single dose of a composition herein also preferably contains from about 5 milligrams to about 1000 milligrams, preferably from about 100 milligrams to about 500 milligrams, of dioctyl sulfosuccinate, preferably calcium or sodium.

D. Optional Ingredients

Compositions of the present invention optionally contain additional ingredients, depending upon the form of the composition and the desired effect and aesthetics. Some compositions, such as solid dose forms, gel capsule forms and food forms, preferably comprise, in addition to the bulk fiber and dioctyl sulfosuccinate, from about 0.1% to about 85%, more preferably from about 30% to about 80%, most preferably from about 50% to about 70%, by weight of the composition, of carrier material. Such carrier material can include flow agents, like fumed silicon dioxide, starches, dextrin, maltodextrins, sweeteners, dispersants, emulsifiers, flavoring, coloring, and contain other fibers, such as oat bran, wheat bran, or rice bran, to add body and flavor.

Psyllium-containing product forms, methods for making, and useful carrier materials are described in, for example, U.S. Pat. No. 4,459,280, Colliopoulos, issued Jul. 10, 1984, U.S. Pat. No. 4,548,806, Colliopoulos, issued Oct. 22, 1985, and U.S. Pat. No. 4,321,263, Powell et al, issued. Mar. 23, 1982, all incorporated herein by reference.

Useful excipients which can be included in pharmaceutical forms herein are described in the American Pharmaceutical Association's *Handbook of Pharmaceutical Excipients,* incorporated herein by reference.

E. Methods for Treating Constipation

The present invention also relates to methods for treating constipation in humans or lower animals. These methods comprise orally administering a safe and effective amount of any of the laxative composition described herein.

By "safe and effective amount" is meant an amount of this laxative composition which is high enough to positively modify the condition being treated, but low enough to avoid serious side effects at a reasonable benefit/risk ratio within the scope of sound medical judgement. The safe and effective amount may vary with the age and physical condition of the person being treated, the severity of the condition, the specific ingredients employed, and like factors.

II. Process of the Present Invention

The present invention is a process for making an ingestible, neutral tasting laxative composition by coating dioctyl sulfosuccinate with a material selected from the group consisting of C14–18 fats, C16–20 fatty acids, polyol polyesters, $C_{-18}$ fats and waxes, pH sensitive polymers, food gums, and combinations thereof. Derivatives of these materials are also included, though not preferred.

By "neutral tasting" is meant that, when ingested, the bitterness of the dioctyl sulfosuccinate is not detected by the person (or lower animal) who is ingesting it (i.e. the taste is not bad). A sugar or other flavor could also be added to the composition to enhance its taste. These compositions are preferably chewable tablets, drink mixes, and food forms.

A. Benefits of Coating

The coating of the present process is advantageous in that the dioctyl sulfosuccinate is prevented from effecting a bad taste in the mouth. The coating can also be chosen so that it remains largely intact through the stomach, thereby avoiding the gastric disturbances which are commonly associated with the use of dioctyl sulfosuccinate as a medicinal drug. The protective coating is chosen so that it is dissolved/melted/digested before reaching the large intestine so that dioctyl sulfosuccinate is available for stool softening action.

For example, a $C_{14-18}$ fat coating on the dioctyl sulfosuccinate is believed to melt in the gastrointestinal tract, releasing the dioctyl sulfosuccinate to soften the stool. Fat micelles are then believed to be digested by pancreatic lipase in the small intestine, and the free fatty acids and monoglycerides thus released are then almost totally absorbed through the wall of the small intestine. In the case of the fat/wax coating, it is believed that when the fat is melted, the wax, which is bound by the fat, is also released. It is likely that the wax is passed through with the stool. In the case of a fatty acid coating, the fatty acids melt in the gastrointestinal tract and the dioctyl sulfosuccinate is then released to act in the intestine. The fatty acids are easily absorbed by the small intestine.

The pH sensitive polymer and gum coatings herein have the advantages of the fat/fatty acid coating. It is believed that the pH sensitive polymer coating does not dissolve until it is in a specific pH environment, preferably the basic environment of the small intestine. It is likely that the pH sensitive polymer is passed through with the stool. The food gums also "melt away" in the gastrointestinal tract, releasing the dioctyl sulfosuccinate for action in the intestine. The gums used for coating herein are polysaccharides which are also broken down by naturally occuring enzymes and absorbed through the intestine.

B. Single or Double Coatings

The coating can be a single coating or multiple coatings. A double coating is preferred. In the preferred double coating, a second coating is selected from the group consisting of $C_{14-18}$ fats, $C_{16-20}$ fatty acids, sucrose polyesters, $C_{14-18}$ fats and waxes, pH sensitive polymers, food gums, and combinations thereof. Although both coatings are selected from among the same materials, the second coating preferably is different from the first coating; the second coating preferably does not have any appreciable amount of material in common with the first. Each coating can be made up of one or more materials from within the same grouping, e.g., a $C_{16}$ triglyceride and a C 18 triglyceride, and/or between groupings, e.g., a C 16 triglyceride and a pH sensitive polymer. However, it is preferred that a single material be used for each coating.

C. Types of Coating Materials

Preferred coating materials are those which are melted, dissolved, removed or digested in the gastrointestinal tract and which do not appreciably alter the dioctyl sulfosuccinate. Preferred are those coating materials which substantially melt or are largely dissolved at or about body temperature. The coating material is preferably below the melting point of the dioctyl sulfosuccinate.

Preferred food gums are selected from the group consisting of starches, cellulose derivatives, guar gum, locust bean gum, pectin, algin, carrageenan, xanthan gum, gum arabic, agar, gum ghatti, karaya, tragacanth, and combinations thereof. Some of these are described in *Industrial Gums: Polysaccharides and their Derivatives*, by R. Whistler and J. BeMiller, Third Edition, incorporated herein by reference (see Chapters 5–8, 13, 18, and 20). Most preferred are cellulose derivatives. Preferred cellulose derivatives are selected from the group consisting of methylcellulose, ethylcellulose, carboxymethylcellulose, hydroxypropyl methylcellulose, hydroxypropyl ethylcellulose, and mixtures thereof.

Preferred $C_{14-18}$ fats herein are trimyristan, tripalmitin, and tristearin. $C_{16}$ and $C_{18}$ fats are preferred. Fats for use herein are preferably solid in the mouth but melt at body temperature. The preferred melting point is between about 95° F. and about 99° F. Also preferred are palmitic, oleic, palmitic triglyceride (POP) and soybean hardstock.

Waxes for inclusion with fats herein are esters of long chain fatty acids and long chain alcohols. Preferred are beeswax, and vegetable waxes. More preferred waxes are selected from the group consisting of jojoba, polyethylene glycol of molecular weight between about 1,000 and about 20,000, preferably between about 5,000 and about 10,000, stearin waxes, sorbitan ester waxes, and mixtures thereof. Most preferred is sorbitan tristearin, preferably with soybean hardstock.

$C_{16}$ to $C_{20}$ fatty acids are palmitic, stearic and arachidic. $C_{16}$ and $C_{18}$ fatty acids and sorbitan esters are preferred.

pH sensitive polymers suitable for use herein are selected from the group consisting of cellulose acetate phthalate (CAP), polymethacrylic acid polymers, and mixtures thereof. Eudragit® S-100 for flavored drink mixes and Eudragit® E (Rohm Pharma) for wafers or beverages are most preferred.

Suitable polyol polyesters (called "Olestra") for use herein are described in U.S. Pat. No. 4,005,196, Jandecek et al, issued Jan. 25, 1977, incorporated herein by reference. Sucrose polyester is preferred.

D. Preferred Processes

There are several preferred processes for coating the dioctyl sulfosuccinate. The most preferred process is (a) melting the coating material under a heat within about 10° F., preferably within about 5° F., of the melting point of the coating material, or substantially dissolving the coating material in a solvent, preferably an organic solvent, most preferably acetone, (b) adding the dioctyl sulfosuccinate to a fluid bed and (c) coating (b) with (a) in the fluid bed. The melted coating material is preferably less than the melting point of the dioctyl sulfosuccinate so that when the dioctyl sulfosuccinate is added, it does not melt. In this way, particles with a core of dioctyl sulfosuccinate surrounded by succeeding layers of coating material are made. This preferred process microencapsulates the dioctyl sulfosuccinate particles, forming larger particles. The fluid bed coating apparatus is preferably a Glatt Powder Coater/Granulator. An even more preferred process is: (a) substantially dissolving the coating material in an organic solvent, (b) adding the dioctyl sulfosuccinate to a fluid bed and (c) coating (b) with the product of (a) in the fluid bed. Most preferably, the dioctyl sulfosuccinate is coated with carboxymethylcellulose and cellulose acetate phthalate. Either one can be the outer coating. Preferably, two successive, different coatings are applied to the dioctyl sulfosuccinate A second preferred process is (a) melting the coating material under a heat within about 10° F., preferably within about 5° F., of the melting point of the coating material, and preferably below the melting point of dioctyl sulfosuccinate, (b) adding the dioctyl sulfosuccinate to the product of step (a), and (c) spray congealing or spray quenching the product of (b); wherein the coating material is selected from the group consisting of $C_{14-18}$ fats, $C_{16-20}$ fatty acids, $C_{14-18}$ fats and waxes, and mixtures thereof. This is believed to be a macroencapsulating process, where particles or flakes of coating material containing smaller particles of dioctyl sulfosuccinate are made. This process involves spray entraining the dioctyl sulfosuccinate in the coating material. It is believed that a matrix of coating material and dioctyl sulfosuccinate is thus formed.

In the more preferred spray congealing process, the product of (b) is preferably sprayed into air, preferably dehumidified, which is at a temperature below the melting point of the coating material, so that solidification into small particles takes place. In the spray quenching step, the product is preferably sprayed, most preferably via nozzle(s), into a liquid, preferably water, which is at a temperature below the melting point of the coating material The air or liquid is most preferably at a temperature more than about 30° F. less, preferably more than about 70° F. less, than the melting point of the coating material. The liquid should not be one which would dissolve the particles formed.

A third preferred process is (a) substantially dissolving the coating material in a solvent, preferably an organic solvent. most preferably acetone, (b) adding the dioctyl sulfosuccinate to the product of step (a), and (c) spray drying. Spray drying is preferably into air which has been heated to a temperature at or above the vaporization temperature of the solvent. The solvent should not be one which dissolves the dioctyl sulfosuccinate. This process involves spray entraining the dioctyl sulfosuccinate in the coating material.

For these processes, the product of step (c) is preferably, in step (d), combined with bulk fiber selected from the group consisting of psyllium, methylcellulose, polycarbophil, calcium polycarbophil, bran, malt soup extract, karaya, guar gum, and mixtures thereof. Then, preferably, a drink mix, chewable tablet, or food form is made from the product of step (d), preferably along with other ingredients commonly used in that form. The final composition is preferably within the scope of the composition invention described herein.

The coating herein preferably (1) completely covers the entire surfaces of all dioctyl sulfosuccinate particles, (2) is of sufficient thickness to delay dioctyl sulfosuccinate release during consumption, and (3) will release in the digestive system to provide the dioctyl sulfosuccinate.

Upon completion of the coating process the particles can be tested for leakage of the dioctyl sulfosuccinate. This leakage preferably should not exceed 20 ppm in 240 milliliters of water per 240 milligram dose.

Plasticizers, such as castor oil, triethylcitrate, and acetylated monoglycerides, are optionally and preferably included in the coating solution. The product of step (b) preferably comprises, by weight: from about 70% to about 95%, more preferably from about 80% to about 90%, of solvent; from about 5% to about 20%, more preferably from about 10% to about 15%, of the coating material; and from about 1% to about 10%, more preferably from about 2% to about 5%, of plasticizer. It most preferably consists essentially of 83–87% solvent; 10–13% barrier material; and 2–4% plasticizer.

The coating materials are preferably coated on the dioctyl sulfosuccinate from the product of step (a) to coating ranges of, by weight, from about 1% to about 50%. The coating materials are more preferably coated on the dioctyl sulfosuccinate from, for example, aqueous solutions, organic solvent solutions or hot melts, to coating ranges of, by weight, preferably from about 5% to about 30%, most preferably from 8% to 20%.

One embodiment of this invention is where the dioctyl sulfosuccinate is coated with pH sensitive celluloses or cellulosic films, waxes, fats, gums, methacrylic acid polymers, acetylated monoglycerides, or combinations thereof, and then included in the composition with the bulk fiber. Possible combinations include dioctyl sulfosuccinate coated with an occlusion hydrophobic fat, wax, or gum, then with a pH sensitive material (e.g., cellulosic or polyacrylic acid polymer). This encapsulated form would preferably be mixed with the bulk fiber in a powdered drink mix, chewable tablet, or a food form.

The following examples illustrate the compositions and processes of the present inventions. They are presented by way of example only and are not to be construed as limiting the scope of these inventions.

All parts, percentages, and ratios used herein are by weight unless otherwise specified. All references cited herein are expressly incorporated by reference.

EXAMPLE I

Drink Mix Composition

A composition of the present invention is as follows. This composition is preferably a drink mix used for the treatment of occasional constipation. The drink mix is mixed with at least 8 oz. of liquid and ingested so as to provide the following amounts of psyllium and dioctyl sodium sulfosuccinate.

| Component | Amount |
| --- | --- |
| Psyllium husk | 5.1 grams |
| Dioctyl sodium sulfosuccinate | 240 milligrams |

The psyllium husk is milled to a small particle size: no more than 4% on 100 mesh and betwen 25% and 50% through 200 mesh, preferably according to U.S. Pat. No. 5,149,541, Leis, Jr. et al, issued Sep. 22, 1992. These psyllium particles are then agglomerated with maltodextrin and citric acid is sprayed on, preferably according to U.S. Pat. No. 4,459,280, Colliopoulos, issued Jun. 10, 1984 and U.S. Pat. No. 5,219,570, Barbera, issued Jun. 15, 1993.

Dioctyl calcium sulfosuccinate, dioctyl potassium sulfosuccinate, can be substituted for the dioctyl sodium sulfosuccinate, or two or three of these can be combined.

Methylcellulose, polycarbophil, calcium polycarbophil, bran, malt soup extract, karaya, guar gum, or mixtures of these can be substituted for the psyllium. The amounts of psyllium and/or dioctyl sulfosuccinate can be varied within the ranges specified herein.

EXAMPLE II

Tablet Composition

A composition of the present invention in the form of a tablet is as follows.

| Material | Weight % |
|---|---|
| Methylcellulose | 76.3 |
| Dioctyl sodium sulfosuccinate | 19.7 |
| Disintegration agent | 4.0 |

These tablets are made by a standard wet granulation process. The tablet target weight is 525 milligrams. The tablet hardness target is 23 SCUs.

Psyllium, polycarbophil, calcium polycarbophil, bran, malt soup extract, karaya, guar gum, or mixtures of these can be substituted for the methylcellulose. The amounts of psyllium and/or dioctyl sulfosuccinate can be varied within the ranges specified herein.

Dioctyl calcium sulfosuccinate, dioctyl potassium sulfosuccinate, can be substituted for the dioctyl sodium sulfosuccinate, or two or three of these can be combined.

EXAMPLE III

Food Wafer Composition

A composition of the present invention in the form of a wafer food is as follows.

| Raw Materials | Weight % |
|---|---|
| Ascorbic acid | 0.15 |
| Natural and artificial flavors | 1.54 |
| Corn oil | 14.80 |
| Cornstarch | 1.97 |
| Fructose crystalline | 6.82 |
| Lecithin oil | 0.99 |
| Molasses granular light | 0.39 |
| Oat hull fiber | 6.42 |
| Psyllium husk | 13.32 |
| Sodium bicarbonate | 0.20 |
| Sucrose white granulated | 17.40 |
| Table oats | 8.89 |
| Water purified USP | Balance |
| Wheat flour | 19.21 |
| Docusate sodium | 0.63 |
| Sorbitan tristearin | 0.20 |

Procedure: In a Hobart bowl add corn oil and lecithin and mix for one minute using speed #1. Note: pre-heat (microwave) lecithin, if necessary. Add psyllium, docusate (which has been coated with the sorbitan tristearin) and mix for one minute using speed #1. Into a separate Hobart bowl, add part of the sucrose, fructose, molasses and half of the water. Mix for 1 minute using Speed #1. Add psyllium/oil/lecithin pre-mix, and oat-fiber. Mix for 1 minute Add rest of water, soda, flavors, ascorbic acid, and starch. Mix for 1 minute w/speed #1. Add flour to the mixer and mix for 1 minute w/speed #1. Record weight of the entire batch and calculate yield. Roll dough into sheets approximately 0.1 inch thick. Cut dough into rectangles of (about 2.5"L×1.6"W). Place bars on baking trays and bake at 375° for 10–12 minutes.

Methylcellulose, polycarbophil, calcium polycarbophil, bran, malt soup extract, karaya, guar gum, or mixtures of these can be substituted for the psyllium. The amounts of psyllium and/or dioctyl sulfosuccinate can be varied within the ranges specified herein.

Dioctyl calcium sulfosuccinate, dioctyl potassium sulfosuccinate, can be substituted for the dioctyl sodium sulfosuccinate, or two or three of these can be combined.

EXAMPLE IV

Tablet Composition

A composition of the present invention in the form of a tablet is as follows.

| Raw Materials | % Wt |
|---|---|
| Psyllium | 71.0 |
| Ethylcellulose | 4.8 |
| Isopropyl alcohol* | — |
| Microcrystalline cellulose | 16.7 |
| PVP** | 1.9 |
| Carnuba wax | 2.3 |
| Docusate sodium | 3.3 |

*dried off during drying process
**cross linked polyvinyl pyrollidone

Procedure: Soak ethylcellulose in isopropyl alcohol overnight. Granulate psyllium with isopropyl/ethylcellulose mixture in mixer. Dry at 49° C. for 3 hours. Mill through 12 mesh screen. Mix in a mixer the following: psyllium, microcrystalline cellulose and carnuba wax. Compress the tablet per granulation specifications using a tableting press. Coat the core tablets.

Methylcellulose, polycarbophil, calcium polycarbophil, bran, malt soup extract, karaya, guar gum, or mixtures of these can be substituted for the psyllium. The amounts of psyllium and/or dioctyl sulfosuccinate can be varied within the ranges specified herein.

Dioctyl calcium sulfosuccinate, dioctyl potassium sulfosuccinate, can be substituted for the dioctyl sodium sulfosuccinate, or two or three of these can be combined.

EXAMPLE V

Fat Co-Melt Process

A process according to the present invention is as follows.

Objective: Coblend dioctyl sodium sulfosuccinate (called docusate sodium), soybean hardstock and sorbitan tristearate in a hot melt, then congeal the blend in cold water and collect the solid particles.

Approach: Raw Materials: Docusate sodium - 99% pure, SIGMA; dioctyl sulfosuccinate Sorbitan tristearate - Famodan® TS by Grindsted Products Soybean hardstock - Durkee Soy I-8

The materials are combined in the following ratios:

| | Weight % |
|---|---|
| Docusate sodium | 25.0 |
| Sorbitan tristearate | 15.0 |
| Soybean hardstock | 60.0 |
| | 100.0 |

These materials are completely melted in a microwave oven. Care is taken to not overheat or scorch the fats. Once melted, the materials are thoroughly mixed. The hot melt is then pumped into a running food processer filled with ice water. The high agitation breaks the melted droplets into small flakes/particles, and the ice water quickly congeals the hot melt. Foaming is likely to occur. The contents of the blender are poured into an 80 mesh sieve and rinsed with cold water. The material is rinsed until no further foaming occurs, which indicates that any docusate remaining on the particles is rinsed away. The resulting particles are fine, irregularly shaped and mostly flakelike in appearance. The particles are air dried.

The experiment can be further refined by varying particle shape, docusate concentration, and types of melted fats. This could reduce surface area thereby reducing the amount of docusate lost during the rinsing step. Surface area may be reduced by changing particle shape and particle size.

EXAMPLE VI

Double Coating Process

A process according to the present invention is as follows.

Objective: Eliminate the bitter taste of dioctyl sodium sulfosuccinate (called docusate sodium) by applying a double coating.

| Coating Material | % Weight | Weight (grams) |
| --- | --- | --- |
| Carboxymethylcellulose | 5 | 125 |
| Water* | 95 | 2375 |

*double distilled, 99.99% pure

Method: Place 2375 milliliters of the water in a 4 liter beaker. Using mechanical stirring (vigorous - - - without incorporating air), slowly add 125 grams of carboxymethylcellulose (CMC). It is best to add the powder as a thin stream that will quickly mix into the water without dumping. Addition time for the 125 grams is 10 minutes. Continue stirring for an additional 20 minutes until the solution is clear. If necessary, store at 4° C.

1st Coat Run:

| Coating Materials | % Weight | Weight (grams) |
| --- | --- | --- |
| Sodium Docusate | 29.4 | 1000 |
| 5% CMC Coating Solution | 70.6 | 2400 |

Method: Clean and assemble a Glatt Fluid bed coater with Wuester coating chamber. Lift into place. Power up the control panel and start the air turbine. Adjust exhaust flap to 26% and set air inlet temp. to 60° C. Allow to run until inlet air is to set temperature. Stop air and lower assembly. Charge Wuester chamber with 1000 grams of sodium docusate. Chamber partition gap is set at about ½ inch. Lift assembly into place and restart air flow. Let run for a few minutes to reach equilibrium and then start pumping the coating solution. Pump at 30 rpm=18 ml/min and an air atomization pressure of 3.2 bar. When run is complete, shut down air and lower assembly. Remove Wuester chamber quickly to avoid contamination of coated product by uncoated powder. Store product in an air tight container at room temperature until next coating step.

2nd Coat Run:

| Coating Materials | Weight (grams) |
| --- | --- |
| Cellulose acetate phthalate (CAP) | 144 |
| Castor Oil | 36 |
| Acetone GR | 1188 |
| Water* | 132 |

*double distilled, deionized; 99.99% pure

Place 1148 grams of acetone in a 4 liter beaker. With mechanical stirring, slowly add 180 grams of CAP. Stir gently until CAP is in solution. Add 45 grams of castor oil with stirring. Finally, slowly add the water to the solution. A precipitate will form but will redissolve into solution. Reweigh the solution and top off with acetone to 1500 grams to make up for acetone evaporation during mixing. Use 1213 grams of coating solution.

Method: Clean and assemble Glatt with Wuester coating chamber. Power up control panel and start turbine and heat inlet air to 50° C. Stop air flow and lower assembly, charge Wuester chamber with 970 grams of CMC coated sodium docusate. Raise assembly and restart air. Allow a few minutes to reach equilibrium. Start pumping coating solution. Pump at 150 rpm=46 mi/min, and an air atomization pressure of 2.84 bar. When run is complete, shut down air and lower assembly. Remove Wooster chamber quickly to avoid contamination of double coated product by single coated product. Store finished product in an air tight container.

EXAMPLE VII

Double Coating Process

A process according to the present invention is as follows.

Objective: Eliminate the negative flavor of dioctyl sodium sulfosuccinate (called docusate sodium) via a double coating, here called barrier (first) and protective (second) coatings.

Approach:

| Raw Materials: | (1) sodium docusate (85%) sodium benzoate (15%) |
| --- | --- |
| | (2) barrier coating |
| | (a) Eudragit S-100 |
| | (b) Eudragit E |
| | (c) Cellulose acetate phthalate (CAP) |
| | (d) Other cellulosic films |
| | (e) Other pH sensitive films |
| | (3) plasticizers |
| | (a) Castor oil |
| | (b) Triethyl citrate |
| | (c) Acetylated monoglycerides |

(Coating Solution: 85% solvent; 12% barrier material; 3% plasticizer)

The sodium docusate is placed in a fluid bed coating apparatus. A solution containing one or more of the barrier coatings named above plus plasticizer is spray coated onto the sodium docusate until it (1) completely covers the entire surfaces of all docusate particles, (2) is of sufficient thickness to delay docusate release during consumption, and (3) will release in the digestive system to provide the dioctyl sulfosuccinate. The coating ranges are expected to be 10 to 25% by weight of the finished coated docusate product.

Upon completion of the coating process the material is tested for leakage. Docusate leakage should not exceed 20 ppm in 240 milliliters of water per 240 milligram dose.

In order to protect the barrier coating during consumption and to provide a means for softening the particles so there is no gritty mouth feel, the coated particles are coated again with a protective coating.

Raw Materials for Protective Coating:
(1) Protective cellulosics
 (A) Methylcellulose
 (B) Carboxymethylcellulose
 (C) Hydroxypropyl methylcellulose or
(2) Protective Waxes/Fats
 (A) Polyethylene glycol
 (B) Sorbitan tristearin/soybean hardstock
 (C) Others These materials can be coated from aqueous solutions or hotmelts to coating ranges of 8 to 20%.

Other processes of the present invention are obtained when other $C_{14-18}$ fats, $C_{16-20}$ fatty acids, sucrose polyesters, $C_{14-18}$ fats and waxes, pH sensitive polymers, food gums, or combinations thereof are substituted for these coating materials.

Having described the various modifications of the present invention, it will appear to those of ordinary skill in the art that various modifications may be made and that such modifications are intended to be within the scope of this invention.

What is claimed is:

1. An ingestible laxative composition comprising, by weight of the composition:
 (a) from about 10% to about 99.99% of bulk fiber selected from the group consisting of psyllium, polycarbophil, calcium polycarbophil, bran, malt soup extract, guar gum, and mixtures thereof, and
 (b) from about 0.0005% to about 25% of dioctyl sulfosuccinate.

2. The composition according to claim 1 comprising from about 10% to about 98% of bulk fiber selected from the group consisting of psyllium, calcium polycarbophil, polycarbophil, and mixtures thereof.

3. The composition according to claim 2 wherein the dioctyl sulfosuccinate is selected from the group consisting of dioctyl sodium sulfosuccinate, dioctyl calcium sulfosuccinate, dioctyl potassium sulfosuccinate, and mixtures thereof.

4. The composition according to claim 3 comprising from about 0.005% to about 10% of dioctyl sulfosuccinate.

5. The composition according to claim 4 which is a single dose composition for relieving constipation.

6. The composition according to claim 5 comprising from about 0.005% to about 15% of dioctyl sodium sulfosuccinate or dioctyl calcium sulfosuccinate.

7. The composition according to claim 6 which is selected from the group consisting of a drink mix, solid dose form, gel capsule form, and a food form.

8. The composition according to claim 7 further comprising from about 0.1% to about 85%, by weight of the composition, of carrier material.

9. The composition according to claim 3 wherein the bulk fiber is psyllium husk comprising particle sizes distributed such that: less than about 15% is greater than about 80 mesh, at least about 45% is within the range of from about 80 mesh to about 200 mesh, and less than about 40% is smaller than about 200 mesh.

10. The composition according to claim 5 wherein the single dose comprises from about 0.5 gram to about 100 grams of psyllium husk, and from about 5 milligrams to about 1000 milligrams of dioctyl sulfosuccinate.

11. The composition according to claim 6 in the form of a drink mix.

12. The composition according to claim 11 comprising from about 50% to about 70% of psyllium husk.

13. The composition according to claim 12 wherein the psyllium husk is agglomerated with maltodextrin and further comprises citric acid which is uniformly dispersed throughout the maltodextrin.

14. The composition according to claim 13 in single dose form and comprising from about 1 to about 10 grams of psyllium husk and from about 100 milligrams to about 500 milligrams of dioctyl calcium or sodium sulfosuccinate or dioctyl sodium sulfosuccinate.

15. The composition according to claim 13 wherein the drink mix consists essentially of from about 4 grams to about 10 grams of psyllium husk, and from about 100 milligrams to about 500 milligrams of dioctyl sulfosuccinate.

16. The composition according to claim 14 wherein the drink mix consists essentially of from about 4.5 grams to about 6 grams of psyllium husk, and from about 200 milligrams to about 300 milligrams of dioctyl calcium sulfosuccinate.

17. A method for treating constipation in humans or lower animals comprising orally administering a safe and effective amount of a laxative composition according to claim 1.

18. A method for treating constipation in humans or lower animals comprising orally administering a safe and effective amount of a laxative composition according to claim 13.

* * * * *